United States Patent [19]

Herr et al.

[11] Patent Number: 4,966,894

[45] Date of Patent: Oct. 30, 1990

[54] POLYSULFATED HEPARINS FOR TREATING DISEASES CAUSED BY RETROVIRUSES

[75] Inventors: Dieter Herr, Altrip; Thomas Doerper, Bissersheim; Lothar Daum, Otterstadt; Karl-Heinz Geiss, Heuchelheim; Achim Moeller, Limburgerhof, all of Fed. Rep. of Germany

[73] Assignee: BASF Aktiengesellschaft, Ludwigshafen, Fed. Rep. of Germany

[21] Appl. No.: 288,444

[22] Filed: Dec. 22, 1988

[30] Foreign Application Priority Data

Dec. 24, 1987 [DE] Fed. Rep. of Germany ....... 3744119

[51] Int. Cl.$^5$ ........................................... A61K 31/725
[52] U.S. Cl. ....................................................... 514/56
[58] Field of Search ........................................... 514/56

[56] References Cited

FOREIGN PATENT DOCUMENTS 240098 1/1987 European Pat. Off. .
270317 11/1987 European Pat. Off. .

OTHER PUBLICATIONS

*The Journal of Biological Chemistry*, vol. 248, No. 18, Sep. 25, 1973, p. 6408.
*Arzneium-Forsch./Drug Res.*, 30(II), Nr. 11 (1980), pp. 1889–1892.
Arch of Aids Research, Band 1, Nr. 1, 1987, Seiten 45–46; N. Yamamoto et al.: "Effect of the Sulfated Polysaccharides on HIV: A Novel Strategy of Chemical Modification for HIV Antivirals".
The Lancet, Band 1, 19, Jun. 1987, Seite 1379; R. Ueno et al.: "Dextran Sulphate, a Potent Anti-HIV Agent in vitro Having Synergism with Zidovudine".
Anticancer Research, Band 7, Nr. 5B, Sep.–Oct. 1987, Seiten 1023–1038; E. De Clercq: "Perspective for the Chemotherapy of AIDS".
Cancer Research, Band 38, Nr. 8, Aug. 1978, Seiten 2401–2407; R. A. DiCioccio et al.: "Inhibition of Deoxynucleotide-Polymerizing Enzyme Activities of Human Cells and of Simian Sarcoma Vir. by Hep.".
Antiviral Research, vol. 7, No. 6, Jul. 1987, 361–367, Elsevier: Masaihiko Ito et al.: "Inhibitory Effect of Dextran Sulfate and Herp. on the Replic. of Human Immuno. Virus (HIV) in Vitro".
The New York Academy of Sciences, Abstracts, Nov. 3–5, 1987, Frederick A. Ofosu, Ph.D. et al.: "Structures and Activities of Heparin and Related Polysaccharides".
Antimicrobial Agents and Chemotherapy, vol. 31, Oct. 1987, No. 10; Robert C. Moellering, Jr. et al.: "Purification and Charac. of an Avian Myeloblastosis and Human Immunodeficiency Virus Reverse . . . ".

*Primary Examiner*—Jerome D. Goldberg
*Attorney, Agent, or Firm*—Oblon, Spivak, McClelland, Maier & Neustadt

[57] ABSTRACT

Polysulfated heparins are used for the preparation of drugs for the prophylaxis and therapy of diseases caused by retroviruses.

5 Claims, No Drawings

POLYSULFATED HEPARINS FOR TREATING DISEASES CAUSED BY RETROVIRUSES

A large number of malignant lymphatic leukemic neoplasias in mice, cattle, birds, monkeys and humans are caused by retroviruses. In particular, acquired immune deficiency syndrome (AIDS) in humans is due to a retrovirus, HIV I (human immunodeficiency virus).

Prophylactic and therapeutic chemical treatment of the stated virus infections in humans and other mammals has attempted to inhibit virus replication by means of, for example, substances which inhibit reverse transcriptase and/or by means of substances which inhibit binding of the retroviruses to the host cell.

Commercial heparin is a selective inhibitor of HIV replication in vitro (Antiviral Res. 7 [1987], 361), but it is unsuitable for antiviral therapy since it has anticoagulant properties and may induce hemorrhages.

It has also been shown (German Laid-Open Application DOS No. 3,601,136) that commercial heparin inhibits reverse transcriptase of Schmidt-Ruppin D (SR-D) virus, an avian retrovirus. This inhibitory action of heparin could not, however, be confirmed for reverse transcriptase of HIV I (Antiviral Res. 7 (1987), 361; Conference on structure and activities of Heparin and related polysaccharides in New York, Abstract 19A, 1987, and own experiments, cf. Table 1, page 6).

The present invention relates to the use of polysulfated heparins for the prophylaxis and therapy of diseases caused by retroviruses.

The present invention furthermore relates to the use of polysulfated heparins for the preparation of drugs for the prophylaxis and therapy of diseases caused by retroviruses.

Polysulfated heparin is heparin which has been additionally sulfated at any free hydroxyl and amino groups, so that the sulfur content is not less than 12.5%. The polysulfated heparin used according to the invention preferably has a sulfur content of from 13 to 15%, in particular from 13.5 to 15%. Polysulfated heparins having a sulfur content of more than 16% are virtually impossible to prepare.

The polysulfated heparin can be used as such or in the form of its salts with physiologically tolerated bases. Salts are, in particular, the Na, Ca and Mg salts. Salts with organic bases, such as diethylamine, triethylamine or triethanolamine, are also suitable. The expression polysulfated heparin, as used here, also includes the salts.

Heparin which is polysulfated can be natural heparin, which has a molecular weight of from 10,000 to 40,000 dalton. By treating natural heperin with nitrite (Biochemistry 15 [1976], 3932), enzymes (Biochem. J. 108 [1968], 647) or a mixture of sulfuric acid and chlorosulfonic acid (French Patent No. 2,538,404), heparins having lower molecular weights are obtained. Polysulfated heparins having a molecular weight of less than 1,000 are not very suitable for controlling retroviruses. Polysulfated heparins having a molecular weight of about 2,000–20,000 are most suitable. The polysulfated heparins having a molecular weight of from 2,000 to 9,000 furthermore have the advantage that they can be administered orally.

The starting substances used for the preparation of polysulfated heparins are unfractionated heparin (UFH) and various low molecular weight heparin fragments obtained by nitrite cleavage (Biochemistry 15 [1976], 3932).

The polysulfation of the various heparins is preferably carried out using chlorosulfonic acid in pyridine as a solvent. For this purpose, the heparins, which are in the form of the alkali metal or alkaline earth metal salts, must be converted into their corresponding pyridinium salt as described below. Preparation of pyridinium heparinate 10 g of unfractionated heparin or 10 g of depolymerized low molecular weight heparin are dissolved in 100 ml of $H_2O$, the solution is poured over a column containing 50 ml of cation exchanger (e.g. DOWEX® MSC-1) and the column is eluted with $H_2O$. The corresponding free heparinic acid appears in the eluate. This acid is then neutralized to pH 7 with about 30 ml of pyridine and the product is then lyophilized. The yield is about 11 g of heparin pyridinium salt.

The pyridinium salts of various heparins, which salts are prepared by the above method, are the starting materials used for the polysulfation. The extent of sulfation is dependent on the amount of chlorosulfonic acid used. The Examples which follow illustrate the preparation of various polysulfated heparins. Polysulfation of UFH 10 g of heparin pyridinium salt were stirred into 50 ml of pyridine while passing in nitrogen and were heated to 50° C. 20 ml of chlorosulfonic acid (2 ml/g of heparin pyridinium salt) were separately added drop-wise to 300 ml of pyridine, while stirring. The temperature of this reaction mixture was 90° C. The pyridine/chlorosulfonic acid mixture was stirred for a short time and then introduced into the initially taken heparin suspension with vigorous stirring. Thereafter, stirring was continued for a further 60 minutes at 50° C. and the mixture was cooled to room temperature.

The granular precipitate was filtered off, washed with methanol and taken up in 100 ml with 0.5% NaCl solution, and precipitation was effected with 600 ml of ethanol. The resulting precipitate was dissolved in $H_2O$, and the pyridine heparin was once again converted into the free heparinic acid over 80 ml of cation exchanger DOWEX® MSC-1. This acid was then brought to pH 7 with 10 N NaOH, and precipitation was then effected with 6 times the volume of ethanol. The sediment was taken up in 100 ml of $H_2O$, the suspension was filtered and the residue was freeze-dried. The yield was 10.8 g; the resulting product (A) had a molecular weight ($\overline{MW}$) of 14,200 dalton and a sulfur content of 14.8%.

Products having the following properties were prepared similarly:
- B. ($\overline{MW}$)=8,200, sulfur content 14.9% (obtained from heparin having a molecular weight of 7,700 dalton)
- C. ($\overline{MW}$)=5,600, sulfur content 14.1% (obtained from heparin having a molecular weight of 5,100 dalton)
- D. ($\overline{MW}$)=4,300, sulfur content 13.6% (obtained from heparin having a molecular weight of 3,800 dalton)
- E. ($\overline{MW}$)=2,800, sulfur content 14.7% (obtained from heparin having a molecular weight of 2,500 dalton)

Compared with heparin or low molecular weight heparin, the products A-E have a negligible anticoagulant action.

Compared with natural heparins or low molecular weight heparins obtained therefrom, the polysulfated heparins have a much higher potential inhibitory action against reverse transcriptase.

This can be shown with the aid of the following tests:

I. Enzyme test with reverse transcriptase from HIV I

In the model system described below, the activity of the reverse transcriptase is determined in the presence of an inhibitor, essentially according to Hansen et al. (J. Biol. Chem. 262 [1987], 12393).

The enzyme test has a total volume of 50 μl and contains the following components: 50 mM tris-HCl pH 7.8, 80 mM KCl, 8 mM $MgCl_2$ and 1 mM DTT. This system contains the synthetic polymer poly(rA)/oligo $(dT)_{15}$ (Boehringer Mannheim) as a matrix, in a concentration of 1 mg/ml. This matrix consists of a synthetic RNA having a length of 100–200 nucleotides, to which short DNA primers having a length of 15 nucleotides are bonded. The DNA primers serve as starting points for the reverse transcriptase. The substrate used in this test is tritium-labeled thymidine triphosphate ($^3$H-dTTP, specific activity 47 Ci/mmol), in a concentration of 100 μ Ci/ml. The enzymatic reaction is started by adding reverse transcriptase and is carried out for 120 minutes at 37° C. The reaction is stopped by adding 5 μl of 0.5 M EDTA solution.

The synthesized DNA is then separated from non-incorporated $^3$H-dTTP molecules by binding to an anion exchanger. For this purpose, the total test mixture is pipetted onto a 3×3 cm DEAE paper and dried. The DNA bound to the DEAE paper is then washed several times in 0.5 M $Na_2HPO_4$ (about 2 l altogether), and then twice more in distilled water and once in ethanol.

The DNA bound to the exchanger is dried under an infrared lamp, after which the activity is determined by liquid scintillation measurement. The unspecific background is the radioactivity bound to the DEAE filter in the absence of reverse transcriptase in the method described above. The unspecific background is about 100 cpm (about 1 o/oo) and is negligible compared with the result of the measurement. The substances to be tested are dissolved in 0.9% strength NaCl solution (1 mg/ml) and the solutions are diluted with distilled water to give a final concentration of 50 μg/ml and 5 μg/ml in the test.

The activity of the reverse transcriptase in the presence of a potential inhibitor is expressed as a percentage of the activity in the absence of an inhibitor; or the inhibitory action of a substance (%) is defined as 100% minus the activity in percent. Table 1 shows the inhibitory actions of the individual compounds at various concentrations.

TABLE 1

| Substance | (MW) | % S | Inhibition % 50 μg/ml |
|---|---|---|---|
| Unfractionated heparin | 13,500 | 12 | 0 |
| Low molecular weight heparin | 7,700 | 12 | 0 |
| Low molecular weight heparin | 3,800 | 12 | 0 |
| A | 14,100 | 14.8 | 98 |
| B | 8,600 | 14.9 | 97 |
| C | 5,600 | 14.1 | 100 |
| D | 4,300 | 13.6 | 90 |
| E | 2,800 | 14.7 | 93 |

II. Cytotoxicity test

Evaluation of the toxicity the novel substances is based on their cytotoxic effects on L929 cells. The cytotoxicity test was carried out as follows:

1. 100 μl of culture medium containing 5×10$^3$ freshly trypsinized L929 cells (ATCC No. CCl 1) in a state of exponential growth were pipetted in the wells of a 96-well flat-base culture plate. The plate was incubated overnight at 37° C. in an incubator. The air in the incubator contained 5% by volume of $CO_2$.

The culture medium contained 500 ml of MEM (=minimum essential medium) with Earle's salts, 50 ml of fetal calf's serum (FCS) heat-inactivated for 30 minutes at 56° C., 5 ml of L-glutamine (200 mM), 2.5 ml of 100× non-essential amino acids, 3 ml of 1 M hepes buffer pH 7.2 and 500 μl of gentamycin (50 mg/ml).

2. On the next day, 100 μl of the substance-containing test solution were added, in a final concentration of 500 μg of substance/ml of culture medium, to the confluent cell cultures, and duplicate serial titer determinations were carried out. A cell control (cells not treated with substance-containing solution) was also run on the culture plate. The culture plate was then incubated for 48 hours at 37° C. in an atmosphere consisting of air with 5% by volume of $CO_2$.

3. The percentage of the surviving cells in the cultures treated with substrate solution was determined by staining with crystal violet. For this purpose, the liquids were removed from the test plate by tapping. 50 μl of crystal violet solutions were pipetted into each well.

The crystal violet solution had the following composition:

3.75 g of crystal violet,
1.75 g of NaCl,
161.5 ml of absolute ethanol and
43.2 ml of 37% strength formaldehyde, the remainder to 500 ml being water which had been purified by filtration over a Millipore-Filter ®, and by ion exchange.

The crystal violet solution remained in the wells for 20 minutes and was then likewise tapped out. The plates were then each washed with 5×300 μl of water per well, in order to remove the dye not bound to cells. The cell-bound dye was extracted from the cells by adding 100 μl of a reagent solution (50% of ethanol, 0.1% of glacial acetic acid and 49.9% of water) to each well. 4 Shaking the plates for 5 minutes gave a uniformly colored solution in each well. To determine the surviving cells, the extinction of the dye solution in the individual wells was measured at 540 nm.

In this test, the novel substances show no cytotoxicity to the L929 cells at concentrations up to 500 μg/ml.

The polysulfated heparinoids can be administered in a conventional manner, orally or parenterally (subcutaneously, intravenously, intramuscularly or intraperimoneally) or as a spray.

The dose depends on the age, condition and weight of the patient and on the route of administration. As a rule, the daily dose of active compound is from about 10 to 1,000 mg/kg body weight for oral administration and from about 0.1 to 10 mg/kg body weight for parenteral administration.

The novel compounds can be used in the conventional solid or liquid pharmaceutical forms, for example as tablets, film tablets, capsules, powders, granules, coated tablets or solutions. These are prepared in a conventional manner and to do so the active ingredients can be mixed with the conventional pharmaceutical excipients, such as tablet binders, fillers, preservatives, tablet disintegrators, flow regulators, plasticizers, wetting agents, dispersants, emulsifiers, solvents, retarding agents, antioxidants and/or propellants (cf. H. Sucker et al.: Pharmazeutische Technologie, Thieme-Verlag, Stuttgart, 1978).

EXAMPLE 1

50 g of product A (sulfur content 14.8%, $\overline{MW}$ 14,200) are dissolved in 5,000 ml of water. The solution is brought to pH 6.5 with 0.1 N sodium hydroxide solution and is rendered blood-isotonic by adding sodium chloride. Ampoules are each filled with 5 ml of this solution and are sterilized.

Ampoules containing products B (sulfur content 14.9%, $\overline{MW}$ 8,200), C (14.1%, 5,600), D (13.6%, 4,300) and E (14.7%, 2,800) are prepared in a similar manner.

EXAMPLE 2

Tablets having the following composition are prepared in a conventional manner:
250 mg of product A,
120 mg of lactose,
60 mg of cellulose,
3 mg of magnesium stearate
52 mg of corn starch and
15 mg of polyvinylpyrrolidone.

We claim:

1. A method of treating a disease caused by a retrovirus, which comprises administering a polysulfated heparin to a patient suffering from said disease in an amount effective for inhibiting replication of said retrovirus in said patient, said polysulfate heparin having a molecular weight in the range of about 2,000–20,000 and having a sulfur content from about 13.5 to 15%.

2. The method according to claim 1, wherein said polysulfated heparin has a molecular weight of from 2000–9000.

3. The method according to claim 1, wherein said polysulfated heparin is in the form of a free acid or in the form of salts with physiologically-acceptable bases.

4. The method according to claim 1, wherein said polysulfated heparin has a molecular weight in the range of 2,800 to 14,100, and a sulfur content in the range of 13.6 to 14.9%.

5. The method according to claim 1, wherein said polysulfated heparin is administered in an amount of about 10 to 1,000 mg/kg body weight for oral administration, and of about 0.1 to 10 mg/kg body weight for parenteral administration.

* * * * *